(12) United States Patent
Van Der Beek et al.

(10) Patent No.: US 9,044,446 B2
(45) Date of Patent: Jun. 2, 2015

(54) METABOLIC IMPRINTING EFFECTS OF STRUCTURED LIPIDS

(75) Inventors: Eline Marleen Van Der Beek, Wageningen (NL); Marieke Abrahamse-Berkeveld, Heteren (NL); Annemarie Oosting, Wageningen (NL); Martine Sandra Alles, Apeldoorn (NL)

(73) Assignee: N.V. Nutricia, Zoetermeer (NL)

( * ) Notice: Subject to any disclaimer, the term of this patent is extended or adjusted under 35 U.S.C. 154(b) by 253 days.

(21) Appl. No.: 13/514,934

(22) PCT Filed: Nov. 30, 2010

(86) PCT No.: PCT/NL2010/050801
§ 371 (c)(1),
(2), (4) Date: Aug. 3, 2012

(87) PCT Pub. No.: WO2011/071371
PCT Pub. Date: Jun. 16, 2011

(65) Prior Publication Data
US 2012/0322756 A1 Dec. 20, 2012

(30) Foreign Application Priority Data

Dec. 11, 2009 (WO) ............... PCT/NL2009/050757

(51) Int. Cl.
*A61K 31/22* (2006.01)
*A61K 31/215* (2006.01)
*A23C 9/20* (2006.01)

(52) U.S. Cl.
CPC .............. *A61K 31/215* (2013.01); *A61K 31/22* (2013.01)

(58) Field of Classification Search
CPC ..... A61K 31/23; A61K 31/22; A61K 31/215; A23C 9/206
See application file for complete search history.

(56) References Cited

U.S. PATENT DOCUMENTS 5,686,491 A * 11/1997 Sherwood ..................... 514/561
2009/0004164 A1 * 1/2009 Speelmans et al. ........ 424/93.45

FOREIGN PATENT DOCUMENTS

| EP | 0 698 078 B1 | 8/1997 | |
| EP | 1 557 096 B1 | 4/2010 | |
| FR | 2927771 A1 | 8/2009 | |
| WO | WO 9426855 A1 * | 11/1994 | ............... C11C 3/10 |
| WO | WO-2006/114791 A1 | 11/2006 | |
| WO | WO-2007/073193 A2 | 6/2007 | |
| WO | WO-2007/073194 A2 | 6/2007 | |
| WO | WO-2009/016632 A1 | 2/2009 | |
| WO | WO-2009/047754 A2 | 4/2009 | |

OTHER PUBLICATIONS

Definition of prevent, Oxford English Dictionary Online, http://dictionary.oed.com/, accessed online Mar. 27, 2010, especially definition 9a. at p. 2.*
Entry for Obesity, Mayoclinic.org, http://www.mayoclinic.org/, accessed online on Apr. 16, 2014.*
Grummer-Strawn et al., Pediatrics, 2004, 113(2), p. e81-e86.*
Harzer et al., Am. J. Clin. Nutr., 1983, 37(4), p. 612-621.*
Clark et al., J. Pediatrics, 1992, 120(4), p. S151-S158.*
Scott, C.E., Nutrafoods, Jul. 2010, 9(3), p. 7-13.*
International Search Report for PCT/NL2010/050801—mailed Jan. 27, 2011.

* cited by examiner

*Primary Examiner* — Jonathan S Lau
(74) *Attorney, Agent, or Firm* — Gilberto M. Villacorta; Sunit Talapatra; Foley & Lardner LLP

(57) ABSTRACT

The invention relates to the use of triglycerides which an enhanced portion of the palmitic acid residues in the sn-2 position for an early in life diet for improving the development of a healthy body composition, in particular prevention of obesity, later in life.

18 Claims, No Drawings

METABOLIC IMPRINTING EFFECTS OF STRUCTURED LIPIDS

CROSS-REFERENCE TO RELATED APPLICATIONS

This application is a National Stage application of PCT/NL2010/050801 filed Nov. 30, 2010, which claims priority from International Application No. PCT/NL2009/050757, filed Dec. 11, 2009. These applications are herein incorporated by reference in their entirety.

FIELD

The present invention relates to the field of infant nutrition and the effect of the lipid component of the diet on the body composition later in life.

BACKGROUND

Breast-feeding is the preferred method of feeding infants. Breast fed infants have a decreased chance of becoming obese later in life, compared to formula fed infants, but little is known about the effects of ingredients in the infant formulae on obesity later in life. Obesity is a major health problem in the Western world. It is a medical condition in which excess fat has accumulated to the extent that it may have an adverse effect on health, leading to reduced life expectancy and it is associated with many diseases, particularly heart disease and type 2 diabetes. Obesity is a leading preventable cause of death worldwide, with increasing prevalence in adults and children, and authorities view it as one of the most serious public health problems of the 21$^{st}$ century. The present invention relates to infant nutrition with a lipid component beneficially effecting the body composition later in life.

WO 2007/073194 relates to infant formulae comprising phospholipids, sphingolipids, and cholesterol for the prevention of obesity.

WO 2007/073193 relates to infant formulae with specific linoleic acid to alpha-linolenic acid ratio's, low linoleic acid content and comprising phospholipids, sphingolipids, cholesterol and/or choline plus uridine for the prevention of obesity later in life.

Infant milk formulae comprise predominantly vegetable oils as lipid source and in vegetable oils the palmitic acid is mainly in the sn-1 and sn-3 position. The pancreatic lipases hydrolyse the palmitic acid and the liberated free palmitic acid easily forms calcium-fatty acid complexes in the intestine, thereby reducing the bioavailability of calcium and palmitic acid and increasing stool hardness.

Synthetic or structured lipids are known comprising more palmitic acid residues in the sn-2 position and their presence in infant formulae increases palmitic acid absorption, calcium absorption and softer stools. Also an increase in bone mass is reported.

EP 0 698 078 discloses triglyceride compositions as obtainable by 1,3-specific enzymic interesterification of a triglyceride mix, comprising over 30% palmitic acid and/or stearic acid, from which over 35% is bonded at the 2 position, while the remaining fatty acid residues are mainly unsaturated.

EP 1 557 096 B1 relates to an improved infant formula resulting in reduced constipation, abdominal discomfort and gastrointestinal problems, which comprises a protein component having a phosphorus content of less than 0.75 g P/100 g protein, and a lipid component that can easily be digested by an infant, comprising fatty acid triglycerides, in which palmitic acid residues make up more than 10% (w/w) of all fatty acid residues present in the triglycerides, at least 30% of the palmitic acid residues in the triglycerides being in the Sn2 position.

SUMMARY OF THE INVENTION

The inventors surprisingly found that administration early in life of a diet comprising triglycerides with an increased portion of the palmitic acid residues esterified on the sn-2 position of the glycerol backbone affects the growth and body composition later in life. When early in life a diet of the present invention that comprised triglycerides with increased palmitic acid residues esterified on the sn-2 position, had been administered, it was observed that later in life the body composition was changed, resulting in less fat mass accumulation, less fat mass relative to total body weight, increased lean body mass, increased body weight and increased muscle tissue compared to the body composition upon administering early in life a control diet with conventional triglycerides, even when the diet consumed later in life was the same in both groups. This decreased fat mass accumulation was observed, even when total body weight accumulation was increased. In particular the visceral adipose tissue relative to subcutaneous adipose tissue was reduced. Visceral obesity is most associated with health problems.

This effect later in life was different from the direct effect on the diet. A slightly lower growth during diet intervention, initially via the mother until day 15, but also thereafter i.e. day 15-31, i.e. (early) infancy was observed whereas at the end of dietary intervention at day 42, an increase in body weight, lean body mass and fat mass, but similar fat mass relative to total body weight, was observed compared to the control diet. Fat mass in young children has important roles in energy storage, insulation, storage of fat soluble vitamins and hormonal development, such as the development of leptin and insulin sensitivity and it is therefore not desired to decrease fat mass in infants and young children. So due to the lipids of the present invention differences in patterns of growth in infancy arised and programmed the body which results in a healthier growth later in life, i.e. adulthood.

The present invention relates to infant formulae or growing up milks for toddlers comprising triglycerides with an increased portion of the palmitic acid residues esterified on the sn-2 position of the glycerol backbone. The present invention therefore can be used for food compositions intended for infants and/or toddlers in order to prevent obesity, visceral obesity, increase lean body mass, increase muscle tissue, decrease relative fat mass and/or decrease fat mass accumulation later in life.

DETAILED DESCRIPTION OF THE INVENTION

The present invention thus concerns a method for preventing obesity, reducing the risk of obesity, and/or treatment of obesity, said method comprising administering to a human subject a composition, said composition not being human milk, and said composition comprising triglycerides comprising at least 10 wt. % of palmitic acid residues based on total fatty acid residues present in the triglycerides, and comprising at least 30 wt. % of the palmitic acid residues in the sn-2 position of the triglyceride based on total palmitic acid residues.

The present invention also concerns a method for improving body composition, the improvement of body composition being selected from the group consisting of increased lean body mass, decreased fat mass relative to total body weight, decreased fat accumulation and increased muscle mass, said method comprising administering to a human subject a composition, said composition not being human milk, and said composition comprising triglycerides comprising at least 10 wt. % of palmitic acid residues based on total fatty acid residues present in the triglycerides, and comprising at least 30 wt. % of the palmitic acid residues in the sn-2 position of the triglyceride based on total palmitic acid residues.

The invention can also be worded as the use of a composition, said composition not being human milk, and said composition comprising triglycerides comprising at least 10 wt. % of palmitic acid residues based on total fatty acid residues present in the triglycerides, and comprising at least 30 wt. % of the palmitic acid residues in the sn-2 position of the triglycerides based on total palmitic acid residues for the manufacture of a composition for prevention of obesity, reducing the risk of obesity, and/or treatment of obesity.

The invention can also be worded as the use of a composition, said composition not being human milk, and said composition comprising triglycerides comprising at least 10 wt. % of palmitic acid residues based on total fatty acid residues present in the triglycerides, and comprising at least 30 wt. % of the palmitic acid residues in the sn-2 position of the triglycerides based on total palmitic acid residues for the manufacture of a composition for improving body composition, the improvement of body composition being selected from the group consisting of increased lean body mass, decreased fat mass relative to total body weight, decreased fat accumulation and increased muscle mass.

The invention can also be worded as a composition, said composition not being human milk, and said composition comprising triglycerides comprising at least 10 wt. % of palmitic acid residues based on total fatty acid residues present in the triglycerides, and comprising at least 30 wt. % of the palmitic acid residues in the sn-2 position of the triglycerides based on total palmitic acid residues for use in prevention of obesity, reducing the risk of obesity, and/or treatment of obesity.

The invention can also be worded as a composition, said composition not being human milk, and said composition comprising triglycerides comprising at least 10 wt. % of palmitic acid residues based on total fatty acid residues present in the triglycerides, and comprising at least 30 wt. % of the palmitic acid residues in the sn-2 position of the triglycerides based on total palmitic acid residues for use in improving body composition, the improvement of body composition being selected from the group consisting of increased lean body mass, decreased fat mass relative to total body weight, decreased fat accumulation and increased muscle mass.

Obesity is considered to be a medical condition and thus prevention of obesity, reducing the risk of obesity, and/or treatment of obesity is seen as a method of treatment of the human body by therapy. However, improving body composition can be considered as not being therapeutic meaning that for all jurisdictions this aspect can be properly worded by the method for improving body composition as specified above.

Obesity

The present composition is preferably administered to a human subject with an age below 36 months, preferably below 18 months, more preferably below 12 months, even more preferably below 6 months. Preferably the human subject is not obese and/or not suffering from overweight.

Obesity in the present invention relates to an excess of body fat mass. Fat mass is also known as adipose tissue or fat tissue. An adult human person suffers from obesity if over 25 wt. % (for man) or over 30 wt. % (for women) of body weight is fat mass. Obesity is sometimes referred to as adiposity.

Suitable ways to determine % body fat mass are underwater weighing, skin fold measurement, bioelectrical impedance analysis, computed tomography (CT/CAT scan), magnetic resonance imaging (MRI/NMR), ultrasonography and dual energy X-ray absorptiometry (DEXA). A preferred method is DEXA measurement. In the context of this invention body fat mass is determined by DEXA.

The increased risk of health problems later in life, such as diabetes and cardiovascular diseases, is related to the occurrence of visceral adiposity and not to general obesity. The term 'visceral obesity' refers to a condition with increased visceral fat tissue. Visceral adiposity is typically caused by (accumulation of) excessive visceral fat tissue. Visceral fat, also known as organ fat, intra-abdominal fat, peritoneal fat or central fat, is normally located inside the peritoneal cavity as opposed to subcutaneous fat which is found underneath the skin and intramuscular fat which is found interspersed in skeletal muscles. Visceral fat includes the abdominal fat surrounding the vital organs and includes mesenteric fat, perirenal fat, retroperitoneal fat and preperitoneal fat (fat surrounding the liver). A waist circumference above 102 cm in adult man or above 88 cm in adult women indicates the presence of visceral adiposity. Hip-waist ratio's exceeding 0.9 in man and 0.85 in women indicate visceral adiposity. For children of 3-19 years old appropriate cutoffs for age- and sex-dependent waist circumferences can be found in Taylor et al, 2000 Am J Clin Nutr 72:490-495. A subject suffers from visceral adiposity when it meets one or more of the above criteria (regarding VAT, waist circumference or waist-hip ratio thresholds).

Lipid Component

Herein LA refers to linoleic acid and/or acyl chain (18:2 n6); ALA refers to α-linolenic acid and/or acyl chain (18:3 n3); LC-PUFA refers to long chain polyunsaturated fatty acids and/or acyl chains comprising at least 20 carbon atoms in the fatty acyl chain and with 2 or more unsaturated bonds; DHA refers to docosahexaenoic acid and/or acyl chain (22:6, n3); EPA refers to eicosapentaenoic acid and/or acyl chain (20:5 n3); ARA refers to arachidonic acid and/or acyl chain (20:4 n6); DPA refers to docosapentaenoic acid and/or acyl chain (22:5 n3). PA relates to palmitic acid and/or acyl chains (C16:0).

The composition that is to be administered according to the present method or use comprises lipids. The lipids include one or more of triglycerides, phospholipids, cholesterol, free fatty acids, mono- and diglycerides. According to the present invention, the composition comprises triglycerides. Triglycerides comprise a glyceride molecule to which, via ester bonds, three fatty acid residues are attached, which may be the same or different, and which are generally chosen from saturated and unsaturated fatty acids containing 6 to 26 carbon atoms, including but not limited to LA, ALA, oleic acid (C18:1), PA and/or stearic acid (C18:0). Such fatty acid triglycerides may differ in the fatty acid residues that are present and/or in the respective position(s) of the fatty acid residues (e.g. in the sn-1, -2 and/or -3 position). The triglycerides used in the present invention for the manufacture of a composition are chosen such that the amount of PA residues that are present in the triglycerides are 10 wt. % or more based on total fatty acid present in the triglycerides, preferably more than 15 wt. %. Preferably the amount of PA residues that are present in the triglycerides are below 30 wt. %, more preferably between 16 and 24%. The triglycerides used in the present invention for the manufacture of a composition are chosen such that of the total PA residues present in the triglyceride at least 30%, preferably at least 35%, more preferably at least 40% are in the sn-2 or beta position of the triglyceride.

The triglyceride of the present invention are commercially available—e.g. from Loders Croklaan under the name Betapol™ and/or can be prepared in a manner known per se, for instance as described in EP 0 698 078 and/or EP 0 758 846. Another suitable source is InFat™ of Enzymotec.

Preferably the amount of the triglyceride with increased amount of palmitic acid residues on the sn-2 position that is comprised in the lipid fraction of the composition that is to be administered according to the present method or use, herebelow also named the final composition, is between 20 and 100 wt. %, more preferably between 50 and 80%. Preferably the amount of the triglyceride with increased amount of palmitic acid residues on the sn-2 position is such that the lipid fraction of the final composition comprises at least 10 wt. %, more preferably at least 15 wt. % of palmitic acid residues based on total fatty acid residues, and comprise at least 15 wt. % of the palmitic acid residues based on total palmitic acid residues in the sn-2 position of the triglyceride, more preferably at least 25 wt. %, more preferably at least 30 wt. %, even more preferably at least 35 wt. %. Preferably the palmitic acid residues in the final composition are below 30 wt. % based on total fatty acids comprised in the lipid fraction.

The lipid provides preferably 30 to 60% of the total calories of the composition. More preferably the present composition comprises lipid providing 35 to 55% of the total calories, even more preferably the present composition comprises lipid providing 40 to 50% of the total calories. When in liquid form, e.g. as a ready-to-feed liquid, the composition preferably comprises 2.1 to 6.5 g lipid per 100 ml, more preferably 3.0 to 4.0 g per 100 ml. Based on dry weight the present composition preferably comprises 10 to 50 wt. %, more preferably 12.5 to 40 wt. % lipid, even more preferably 19 to 30 wt. % lipid. The lipid comprises preferably from 80 to 100 wt. % triglycerides based on total lipid, more preferably 90 to 100 wt. %.

The lipid of the present invention preferably comprises vegetable lipids. The presence of vegetable lipids advantageously enables an optimal fatty acid profile, high in (poly) unsaturated fatty acids and/or more reminiscent to human milk fat. Using lipids from cow's milk alone, or other domestic mammals, does not provide an optimal fatty acid profile. This less optimal fatty acid profile, such as a large amount of saturated fatty acids, is known to result in increased obesity. Preferably the present composition comprises at least one, preferably at least two lipid sources selected from the group consisting of linseed oil (flaxseed oil), rape seed oil (such as colza oil, low erucic acid rape seed oil and canola oil), salvia oil, perilla oil, purslane oil, lingonberry oil, sea buckthorn oil, hemp oil, sunflower oil, high oleic sunflower oil, safflower oil, high oleic safflower oil, olive oil, black currant seed oil, echium oil, coconut oil, palm oil and palm kernel oil. Preferably the present composition comprises at least one, preferably at least two lipid sources selected from the group consisting of linseed oil, canola oil, coconut oil, sunflower oil and high oleic sunflower oil. When in liquid form, e.g. as a ready-to-feed liquid, the composition preferably comprises 2.1 to 6.5 g vegetable lipid per 100 ml, more preferably 3.0 to 4.0 g per 100 ml. Based on dry weight the present composition preferably comprises 10 to 50 wt. %, more preferably 12.5 to 40 wt. % vegetable lipid, even more preferably 19 to 30 wt. %. Preferably the composition comprises 50 to 100 wt. % vegetable lipids based on total lipids, more preferably 70 to 100 wt. %, even more preferably 75 to 97 wt. %. It is noted therefore that the present composition also may comprise non-vegetable lipids.

LA preferably is present in a sufficient amount in order to promote a healthy growth and development, yet in an amount as low as possible to prevent occurrence of obesity later in life. The composition therefore preferably comprises less than 15 wt. % LA based on total fatty acids, preferably between 5 and 14.5 wt. %, more preferably between 6 and 10 wt. %. Preferably the composition comprises over 5 wt. % LA based on fatty acids. Preferably ALA is present in a sufficient amount to promote a healthy growth and development of the infant. The present composition therefore preferably comprises at least 1.0 wt. % ALA based on total fatty acids. Preferably the composition comprises at least 1.5 wt. % ALA based on total fatty acids, more preferably at least 2.0 wt. %. Preferably the composition comprises less than 10 wt. % ALA, more preferably less than 5.0 wt. % based on total fatty acids. The weight ratio LA/ALA should be well balanced in order to prevent obesity, while at the same time ensuring a normal growth and development. Therefore, the present composition preferably comprises a weight ratio of LA/ALA between 2 and 15, more preferably between 2 and 7, more preferably between 4 and 7, more preferably between 3 and 6, even more preferably between 4 and 5.5, even more preferably between 4 and 5.

Preferably the composition comprises less than 10 wt. % short chain fatty acids based on total fatty acids, preferably less than 5 wt. %, preferably less than 2 wt. %. Short chain fatty acids are fatty acids with an acyl chain of 2 to 5. Preferably the composition comprises less than 30 wt. % medium chain fatty acids based on total fatty acids, preferably less than 20 wt. %, preferably less than 15 wt. %. Medium chain fatty acids are fatty acids with an acyl chain of 6 to 12.

Nutritional Composition

The composition preferably comprises digestible carbohydrate. The digestible carbohydrate preferably provides 30 to 80% of the total calories of the composition. Preferably the digestible carbohydrate provides 40 to 60% of the total calories. When in liquid form, e.g. as a ready-to-feed liquid, the composition preferably comprises 3.0 to 30 g digestible carbohydrate per 100 ml, more preferably 6.0 to 20, even more preferably 7.0 to 10.0 g per 100 ml. Based on dry weight the present composition preferably comprises 20 to 80 wt. %, more preferably 40 to 65 wt. % digestible carbohydrates.

Preferred digestible carbohydrate sources are lactose, glucose, sucrose, fructose, galactose, maltose, starch and maltodextrin. Lactose is the main digestible carbohydrate present in human milk. The present composition preferably comprises lactose. The present composition preferably comprises digestible carbohydrate, wherein at least 35 wt. %, more preferably at least 50 wt. %, more preferably at least 75 wt. %, even more preferably at least 90 wt. %, most preferably at least 95 wt. % of the digestible carbohydrate is lactose. Based on dry weight the present composition preferably comprises at least 25 wt. % lactose, preferably at least 40 wt. %.

Preferably the present composition comprises non-digestible oligosaccharides with a degree of polymerization (DP) between 2 and 250, more preferably 3 and 60. The non-digestible oligosaccharides advantageously prevent the onset of insulin resistance, which also will result in a reduced obesity and/or fat mass later in life. Furthermore, the presence of non-digestible oligosaccharides advantageously results in an intestinal microbiota low in Firmicutes and high in Bacteroidetes, which results in a reduced obesity. Therefore the non-digestible oligosaccharides are presumed to enhance the anti-obesity effects of the larger lipid globules of the composition according to the present invention.

Preferably the present composition comprises fructo-oligosaccharides, galacto-oligosaccharides and/or galacturonic acid oligosaccharides, more preferably galacto-oligosaccharides, most preferably transgalacto-oligosaccharides. In a preferred embodiment the composition comprises a mixture of transgalacto-oligosaccharides and fructo-oligosaccharides.

Preferably, the composition comprises of 80 mg to 2 g non-digestible oligosaccharides per 100 ml, more preferably 150 mg to 1.50 g, even more preferably 300 mg to 1 g per 100 ml. Based on dry weight, the composition preferably comprises 0.25 wt. % to 20 wt. %, more preferably 0.5 wt. % to 10 wt. %, even more preferably 1.5 wt. % to 7.5 wt. %. A lower amount of non-digestible oligosaccharides will be less effective in preventing obesity, whereas a too high amount will result in side-effects of bloating and abdominal discomfort.

The present composition preferably comprises proteins. The protein component preferably provides 5 to 15% of the total calories. Preferably the present composition comprises a protein component that provides 6 to 12% of the total calories. More preferably protein is present in the composition below 9% based on calories, more preferably the composition comprises between 7.2 and 8.0% protein based on total calories, even more preferably between 7.3 and 7.7% based on total calories. A low protein concentration advantageously ensures a lower insulin response, thereby preventing proliferation of adipocytes in infants. Human milk comprises a lower amount of protein based on total calories than cow's milk. The protein concentration in a nutritional composition is determined by the sum of protein, peptides and free amino acids. Based on dry weight the composition preferably comprises less than 12 wt. % protein, more preferably between 9.6 to 12 wt. %, even more preferably 10 to 11 wt. %. Based on a ready-to-drink liquid product the composition preferably comprises less than 1.5 g protein per 100 ml, more preferably between 1.2 and 1.5 g, even more preferably between 1.25 and 1.35 g.

The source of the protein should be selected in such a way that the minimum requirements for essential amino acid content are met and satisfactory growth is ensured. Hence protein sources based on cows' milk proteins such as whey, casein and mixtures thereof and proteins based on soy, potato or pea are preferred. In case whey proteins are used, the protein source is preferably based on acid whey or sweet whey, whey protein isolate or mixtures thereof and may include α-lactalbumin and β-lactoglobulin. More preferably, the protein source is based on acid whey or sweet whey from which caseino-glyco-macropeptide (CGMP) has been removed. Preferably the composition comprises at least 3 wt. % casein based on dry weight. Preferably the casein is intact and/or non-hydrolyzed.

The present composition is preferably particularly suitable for providing the daily nutritional requirements to a human with an age below 36 months, particularly an infant with the age below 24 months, even more preferably an infant with the age below 18 months, most preferably below 12 months of age. Hence, the nutritional composition is for feeding or is used for feeding a human subject. The present composition comprises a lipid, and preferably a protein and preferably a digestible carbohydrate component wherein the lipid component preferably provides 30 to 60% of total calories, the protein component preferably provides 5 to 20%, more preferably 5 to 15 wt. %, of the total calories and the digestible carbohydrate component preferably provides 25 to 75% of the total calories. Preferably the present composition comprises a lipid component providing 35 to 50% of the total calories, a protein component providing 6 to 12% of the total calories and a digestible carbohydrate component providing 40 to 60% of the total calories. The amount of total calories is determined by the sum of calories derived from protein, lipids and digestible carbohydrates.

The present composition is not human breast milk. The present composition comprises vegetable lipids. The composition of the invention preferably comprises other ingredients, such as vitamins, minerals according to international directives for infant formulae.

In order to meet the caloric requirements of the infant, the composition preferably comprises 50 to 200 kcal/100 ml liquid, more preferably 60 to 90 kcal/100 ml liquid, even more preferably 60 to 75 kcal/100 ml liquid. This caloric density ensures an optimal ratio between water and calorie consumption. The osmolarity of the present composition is preferably between 150 and 420 mOsmol/l, more preferably 260 to 320 mOsmol/l. The low osmolarity aims to reduce the gastrointestinal stress. Stress can induce adipocyte formation.

Preferably the composition is in a liquid form, with a viscosity below 35 mPa·s, more preferably below 6 mPa·s as measured in a Brookfield viscometer at 20° C. at a shear rate of 100 s$^{-1}$. Suitably, the composition is in a powdered from, which can be reconstituted with water to form a liquid, or in a liquid concentrate form, which should be diluted with water. When the composition is in a liquid form, the preferred volume administered on a daily basis is in the range of about 80 to 2500 ml, more preferably about 450 to 1000 ml per day.

Infant

Adipocytes proliferate during the first 36 months of life as well as more limited in puberty. The amount of adipocytes is an important determinant in the degree of fat mass, adipose tissue and/or obesity later-in-life. Hence the present composition is preferably administered to the human subject during the first 3 years of life. In one embodiment of the use according to the present invention, the nutritional composition is for feeding a human subject with an age between 0 and 36 months. It was found that there is a predominance of proliferation of adipocytes in the first 12 months of life with an optimum in perinatal adipocyte proliferation. Hence, it is particularly preferred that the present composition is administered to a human subject in this period of life. The present composition is therefore advantageously administered to a human of 0-24 months, more preferably to a human of 0-18 months, most preferably to a human of 0-12 months. The present invention particularly aims to prevent obesity later-in-life and is preferably not an obesity treatment. Hence, the present composition is preferably administered to an infant and/or toddler not suffering from obesity or overweight. In one embodiment of the use according to the present invention, the nutritional composition is for feeding a non-obese human subject. Preferably the composition is to be used in infants having a weight appropriate for gestational age.

Although the adipocyte proliferation is most pronounced during the first 36 months of life and puberty, adipocytes are formed also to a lesser degree in the interval between 36 months and puberty. So in one embodiment the present composition is preferably administered to an age up to 5 years, more preferably up to 10 years, more preferably up to 13 years.

Application

The present composition is preferably administered orally to the infant. The present invention also aims to prevent the occurrence of obesity and/or reduce the fat mass at the age above 36 months. In one embodiment the present method is for preventing obesity, reducing the risk of obesity and/or for improving body composition of a human subject when said human subject has an age above 36 months, preferably when said human subject has an age above 5 years, particularly above 13 years, more particularly above 18 years. In one embodiment the present method or the present nutritional composition is for feeding a human subject with an age between 0 and 36 months and for preventing obesity, reducing the risk of obesity and/or for improving body composition when said human subject has an age above 36 months, preferably to prevent obesity, reduce the risk of obesity and/or improve body composition at the age above 5 years, particularly above 13 years, more particularly above 18 years. In one embodiment the prevention of obesity, reduction of the risk of obesity and/or improving of body composition occurs later in life. With later in life is meant an age exceeding the age at which the diet is taken, preferably exceeding said age with at least one year. In one embodiment the present method or the present nutritional composition is for preventing visceral obesity and/or for reducing the ratio visceral fat to subcutaneous fat.

The inventors surprisingly found that when mice during infancy and childhood were fed a food composition comprising triglycerides with palmitic acid residues located in an increased amount at the sn-2 position of the triglyceride, a different and significant effect on body composition later in life was observed compared to mice which during infancy and childhood had been fed a food composition having a similar fatty acid composition, but less palmitic acid residues located on the sn-2 position. At day 42, which is a time point corresponding to childhood in a human setting, on the other hand, the direct of the diet was different in that the mice receiving the diet with triglycerides of the present invention had a higher body weight, fat mass and lean body mass.

A slightly lower growth during diet intervention, initially via the mother until day 15, but also thereafter i.e. day 15-31, i.e. (early) infancy was observed whereas at the end of dietary intervention at day 42, an increase in body weight, lean body mass and fat mass, but similar fat mass relative to total body weight, was observed compared to the control diet. This can be regarded as catch up growth. Catch up growth early in life is generally seen as a risk factor for later in life adiposity, but with the experimental diet this surprisingly did not seem to be the case. So the composition of the present invention is advantageously used in preterm infants or small for gestational age (SGA) infants, in particular for feeding a preterm infant or an infant small for gestational age. A preterm or premature infant relates to an infant born before the standard period of pregnancy is completed before or on 37 weeks pregnancy of the mother, i.e. before or on 37 weeks from the beginning of the last menstrual period of the mother. SGA babies are those whose birth weight lies below the 10th percentile for that gestational age. Premature and/or SGA infants include low birth weight infants (LBW infants), very low birth weight infants (VLBW infants), and extremely low birth weight infants (ELBW infants). LBW infants are defined as infants with a weight less than 2500 g. VLBW infants as infants with a weight which is less than 1500 g, and ELBW infants as infants with a weight less than 1000 g.

At day 98, which is a time point corresponding to early adulthood in humans, the mice, which had previously consumed the food composition of the present invention before turning to the Western style diet for 56 days, had a significantly lower fat mass accumulated and lower percentage fat mass based on body weight and increase muscle tissue than mice which had received a control composition during infancy. The total body weight and lean body mass was increased in the mice fed the experimental diet in early life. It was also surprisingly found that compared to the control diet, administering a diet comprising triglycerides with palmitic acid residues located in an increased amount at the sn-2 position of the triglyceride during infancy resulted in a specific decrease of visceral adipose tissue to subcutaneous adipose tissue later in life. This is advantageous, since in particular visceral adipose tissue is most associated with health problems.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

EXAMPLES

Example 1

Effects of Structured Lipids on Growth and Body Composition Later in Life

An experiment was performed wherein the effects of an IMF with standard vegetable lipid was compared with IMF wherein the lipid component comprises structured triglycerides with an increased amount of palmitic acid in the sn-2 position.

C57/BL6 dams and their offspring were exposed to the diet from day 2 on. The offspring started eating the diet themselves from day 15 onward. They were completely fed on the diet from day 21 on. The experimental weaning diets were continued until day 42. From day 42 to day 98 all pups were fed the same diet based on AIN-93G diet with an adjusted lipid fraction (containing 10 wt. % lipid of which 50 wt. % lard and 1% cholesterol, based on total lipid), which is representative for a Western style diet.

The experimental diets that were used for weaning were:

1) A rodent diet based on AIN-93G protein, carbohydrates and fibre. Additionally the diet comprised 7 wt. % fat being a mixture of palm oil, coconut oil, rapeseed oil, sunflower oil, and high oleic acid sunflower oil. Typically such vegetable oils comprise only 7.5 wt. % of total palmitic fatty acid residues in the sn-2 position.

2) A rodent diet based on AIN-93G protein, carbohydrates and fibre. Additionally the diet comprised 7 wt. % fat with 30 wt. % based on total fat of a mixture of vegetable oil and 70 wt % based on total fat of Betapol™ 45 (Lipid Nutrition, The Netherlands) wherein about 45% of the total palmitic acid is esterified in the sn-2 position of the triglyceride. The amount of palmitic acid in Betapol™ 45 was about 23 wt. % based on total fatty acid residues.

The triglyceride content in both diets was over 98 wt. % based on total lipids. The fatty acid composition of the diets is given in Table 1 and was very similar.

At day 42, all mice switched to a "Western style diet" comprising 10 wt. % lipid until day 98. The fatty acid composition of the Western style diet is also shown in Table 1.

TABLE 1

Fatty acid composition of the diets

|       | Diet 1, Control | Diet 2 | Western Style diet |
|-------|-----------------|--------|--------------------|
| C12:0 | 11.5            | 11.5   | 5.3                |
| C14:0 | 4.6             | 4.3    | 2.7                |
| C16:0 | 17.1            | 17.1*  | 23.1               |

TABLE 1-continued

Fatty acid composition of the diets

| | Diet 1, Control | Diet 2, | Western Style diet |
|---|---|---|---|
| C18:0 | 3.0 | 2.8 | 9.0 |
| C18:1 n-9 | 36.0 | 38.7 | 40.5 |
| C18:2 n-6 (LA) | 14.0 | 14.0 | 11.9 |
| C18:3 n-3 (ALA) | 2.6 | 2.6 | 1.3 |
| Others | 11.2 | 9.3 | 6.7 |

*about 35-45 wt. % of palmitic acid residues at the sn-2 position of the triglycerides.

The mice were weighed twice a week. The food intake was determined once a week during the entire experiment. To determine body composition (i.e., BMC, BMD, fat mass (FM) and fat-free mass (FFM)) DEXA scans (Dual Energy X-ray Absorbiometry) were performed under general anesthesia at day 42, 70, and 98 days after birth respectively, by densitometry using a PIXImus imager (GE Lunar, Madison, Wis., USA). At the age of 98 days the male mice were sacrificed and fat tissues and organs were weighted.

Interestingly, the mice of both diets showed a different growth pattern during dietary intervention. Based on mean litter weight, and after day 21, mean body weight, the experimental group showed less (but non-significant) weight compared to the control group between day 2 and day 31. From day 37 to day 42 mean body weight of pups fed the experimental diet, started to be higher than the control group.

The results are shown in table 2. On day 42 a direct diet effect of the structured lipid was observed in that body weight, lean body mass and fat mass were increased in the mice consuming the lipid of the present invention.

TABLE 2

Body weight Bone mineral Content, Bone Mass density, Fat mass and relative fat mass.

| | Day | Diet 1 | Diet 2 |
|---|---|---|---|
| Body weight | 42 | 23.8 (0.55) | 24.7 (0.63) |
| | 70 | 26.8 (0.72) | 30.3 (0.86)* |
| | 98 | 28.1 (0.67) | 31.8 (1.49)* |
| | 98-42 | 4.3 (0.27) | 7.1 (1.5) |
| Lean body mass | 42 | 18.0 (0.81) | 20.7 (0.41) |
| | 70 | 20.0 (0.33) | 22.7 (0.54)* |
| | 98 | 21.3 90.48) | 22.9 (0.77)* |
| | 98-42 | 3.4 90.53) | 2.3 (0.33) |
| Bone mineral content | 42 | 0.410 (0.013) | 0.411 (0.010) |
| | 70 | 0.504 (0.008) | 0.535 (0.014) |
| | 98 | 0.557 (0.016) | 0.583 (0.18) |
| | 98-42 | 0.147 90.011) | 0.178 (0.012) |
| Bone mineral density | 42 | 0.045 (0.001) | 0.046 (0.001) |
| | 70 | 0.053 (0.001) | 0.054 (0.001) |
| | 98 | 0.053 (0.001) | 0.055 (0.001) |
| | 98-42 | 0.008 (0.000) | 0.010 (0.001) |
| Fat mass | 42 | 3.7 (0.22) | 4.3 (0.14) |
| | 70 | 5.1 (0.22) | 5.9 (0.44) |
| | 98 | 5.1 (0.23) | 5.4 (0.62) |
| | 98-42 | 1.4 (0.25) | 1.1 (0.51) |
| % Fat mass | 42 | 17.0 (0.39) | 17.6 (0.57) |
| | 70 | 20.3 (0.57) | 20.4 (0.91) |
| | 98 | 19.2 (0.78) | 18.8 (1.33) |
| | 98-42 | 2.3 (0.57) | 0.9 (0.75) |

Interestingly, the increased body weight and lean body mass compared to the control mice was maintained later in life, even when the diet was similar. Also an increased bone mineral content was observed later in life.

Unexpectedly, the increase in fat mass and fat % was much lower and at day 98 a decreased % fat mass was observed compared to control mice. Less fat mass has accumulated during the period the mice were on western style diet, despite a higher body weight. Hence, under the same dietary conditions, a healthier body composition later in life is achieved when it is preceded by an improved growth (affecting lean body mass and fat mass) at the end of infancy, i.e. the body is beneficially imprinted during infancy for a healthier growth later in life. Reduced growth very early in life is generally seen as a risk factor for later adiposity, but with the experimental diet this surprisingly did not seem to be the case.

Immediately after the final DEXA measurement on PN day 98, dissection was performed. Organs and white adipose tissue (Epididymal, Peri-renal, Inguinal (Subcutaneous) and retroperitoneal fat) were removed and weighed. Results are shown in table 3. The muscle tissue was significantly higher in mice fed during infancy the diet of the present invention than in control mice.

TABLE 3

Fat tissue and organ weights.

| | Diet 1 | Diet 2 |
|---|---|---|
| Epididymal fat g (mean s.e.) | 0.561 (0.036) | 0.660 (0.065) |
| Subcutaneous fat g (mean s.e.) | 0.278 (0.015) | 0.356 (0.039) |
| Peri-renal fat g (mean s.e.) | 0.031 (0.004) | 0.039 (0.007) |
| Retroperitoneal fat g (mean s.e.) | 0.125 (0.016) | 0.182 (0.025) |
| Ratio epi + peri + retro/sub | 2.21 | 2.14 |
| Liver g (mean s.e.) | 1.316 (0.055) | 1.348 (0.178) |
| Pancreas g (mean s.e.) | 0.174 (0.010) | 0.203 (0.019) |
| Brain g (mean s.e.) | 0.428 (0.003) | 0.434 (0.005) |
| Muscle tibialis g (mean s.e.) | 0.042 (0.002) | 0.050 (0.002)* |

*$P < 0.05$

Example 2

IMF with Structured Lipids

An infant formula for infants of 0 to 6 months comprising per 100 ml 66 kcal, 1.3 g protein (cow's milk protein, whey protein and casein in a weight ratio of 6:4), 7.3 g digestible carbohydrates (mainly lactose), 3.5 g lipid, 0.8 g non-digestible oligosaccharides (galacto-oligosaccharides and polyfructose), minerals, trace elements, vitamins, carnitine, choline, myo-inositol, and taurine as known in the art.

The lipid composition is the same as in diet 2 of example 1.

The infant formula is claimed to prevent fat mass accumulation later in life.

The invention claimed is:

1. A method for reducing the risk of obesity, and/or treating obesity, comprising administering a human subject in need thereof a nutritional composition comprising an effective amount of triglycerides, wherein the triglycerides comprise at least 10 wt. % of palmitic acid residues, based on total fatty acid residues present in the triglycerides, wherein at least 30 wt. % of the palmitic acid residues are in the sn-2 position of the triglycerides, based on total palmitic acid residues, and wherein the composition does not comprise human milk.

2. The method according to claim 1, wherein the human subject is between 0 and 36 months of age.

3. The method according to claim 1, wherein the nutritional composition is administered to a human subject with an age between 0 and 36 months and obesity or its risk is reduced in the human subject at an age above 36 months.

4. The method according to claim 1, wherein the nutritional composition is administered to a human subject with an age between 0 and 36 months and obesity or its risk is reduced in the human subject at an age above 5 years.

5. The method according to claim 1, wherein the human subject is non-obese.

6. The method according to claim 1, wherein the human subject is a preterm infant or an infant small for gestational age.

7. The method according to claim 1, wherein the composition comprises 10 to 50 wt. % lipids based on dry weight of the total composition and wherein the lipid comprises from 80 to 100 wt. % triglycerides based on total lipid.

8. The method according to claim 7, wherein the lipids comprise linoleic acid and alpha-linolenic acid at a linoleic acid to alpha-linolenic acid weight ratio between 4 and 7.

9. The method according to claim 1, wherein the composition comprises lipids, digestible carbohydrates, and proteins, wherein said lipids provide 30 to 60% of the total calories, said protein provides 5 to 20% of the total calories and said digestible carbohydrates provide 25 to 75% of the total calories.

10. The method according to claim 1, wherein the composition further comprises non-digestible oligosaccharides.

11. A method for increasing lean body mass, decreasing fat mass relative to total body weight, decreasing fat accumulation and/or increasing muscle mass, the method comprising administering to a human subject in need thereof a composition comprising an effective amount of triglycerides, wherein the triglycerides comprise at least 10 wt. % of palmitic acid residues, based on total fatty acid residues present in the triglycerides, wherein at least 30 wt. % of the palmitic acid residues are in the sn-2 position of the triglycerides, based on total palmitic acid residues, and wherein the composition does not comprise human milk.

12. The method according to claim 11, wherein the human subject is between 0 and 36 months of age.

13. The method according to claim 11, wherein the nutritional composition is administered to a human subject with an age between 0 and 36 months and lean body mass is increased, fat mass relative to total body weight is decreased, fat accumulation is decreased and/or muscle mass is increased in the human subject at an age above 36 months.

14. The method according to claim 11, wherein the nutritional composition is administered to a human subject with an age between 0 and 36 months and obesity or its risk is reduced in the human subject at an age above 5 years.

15. The method according to claim 11, wherein the composition comprises 10 to 50 wt. % lipids based on dry weight of the total composition and wherein the lipid comprises from 80 to 100 wt. % triglycerides based on total lipid.

16. The method according to claim 15, wherein the lipids comprise linoleic acid and alpha-linolenic acid at a linoleic acid to alpha-linolenic acid weight ratio between 4 and 7.

17. The method according to claim 11, wherein the composition comprises lipids, digestible carbohydrates, and proteins, wherein said lipids provide 30 to 60% of the total calories, said protein provides 5 to 20% of the total calories and said digestible carbohydrates provide 25 to 75% of the total calories.

18. The method according to claim 11, wherein the composition further comprises non-digestible oligosaccharides.

* * * * *